United States Patent [19]
Wagner et al.

[11] 3,980,653
[45] Sept. 14, 1976

[54] PROCESS FOR THE PRODUCTION OF 3,6-BIS-(2-METHYLMERCAPTOETHYL)-2,5-PIPERAZINEDIONE

[75] Inventors: Hans Wagner, Constance; Alfred Maierhofer, Allensbach, both of Germany

[73] Assignee: Deutsche Gold- und Silber-Scheideanstalt vormals Roessler, Germany

[22] Filed: June 26, 1975

[21] Appl. No.: 590,821

[30] Foreign Application Priority Data
June 26, 1974 Germany.......................... 2430617

[52] U.S. Cl............................ 260/268 DK; 424/250
[51] Int. Cl.²........................................ C07D 241/00

[58] Field of Search .............................. 260/268 DK

[56] References Cited
FOREIGN PATENTS OR APPLICATIONS
1,166,201   3/1964   Germany

*Primary Examiner*—Nicholas S. Rizzo
*Assistant Examiner*—Jose Tovar
*Attorney, Agent, or Firm*—Cushman, Darby & Cushman

[57] ABSTRACT

3,6-bis-(2-methylmercaptoethyl)-2,5-piperazinedione is prepared from 5-(2-methylmercaptoethyl)-hydantoin in the presence of water at 100° to 200°C. at elevated pressure.

12 Claims, No Drawings

PROCESS FOR THE PRODUCTION OF 3,6-BIS-(2-METHYLMERCAPTOETHYL)-2,5-PIPERAZINEDIONE

The invention is directed to a process for the production of 3,6-bis-(2-methylmercaptoethyl)-2,5-piperazinedione. This compound is useful for example as an antioxidant for mineral oils, as an anti-ager for rubber and especially as a starting material for the production of the fodder additive methionylmethionine.

It is known to produce piperazinediones from the corresponding aminoacids or the esters of these aminoacids. The reaction is generally carried out by heating the aminoacids or their esters, in a given case in suitable solvents (Elderfield, Heterocyclic Compounds, John Wiley & Sons, New York, 1957 Vol. 6 pages 437–438).

The aminoacids are also converted to the piperazinediones under pressure at temperatures above 150°C. in the presence of carbon dioxide, ammonia and water (Netherlands published application No. 6,714,031). In all of the known processes the yields are relatively small.

There has now been discovered a process for the production of 3,6-bis-(2-methylmercaptoethyl)-2,5-piperazinedione by transformation of 5-(2-methylmercaptoethyl)-hydantoin in the presence of water at temperatures of about 100° to 200°C. and at an elevated pressure.

While according to the known processes for the production of 3,6-bis-(2-methylmercaptoethyl)-2,5-piperazinedione the aminoacid, methionine, or esters of methionine are necessary as starting materials, first the methionine or esters of methionine must be produced in the customary way from 5-(2-methylmercaptoethyl)-hydantoin, in contrast in accordance with the process of the invention the 5-(2-methylmercaptoethyl)-hydantoin is converted directly into the 3,6-bis-(2-methylmercaptoethyl)-2,5-piperazinedione. Surprisingly thereby there are produced higher yields of the piperazinedione than in the reaction of methionine or the esters of methionine.

The reaction of hydantoin to the piperazinedione according to the invention takes place in the presence of water suitable at temperatures of about 100° to 200°C. preferably at temperatures between 140° and 180°C., at elevated pressure. Although any elevated pressure can be employed, advantageously the pressure is so regulated that it is at least 0.2 bar, especially about 0.5 to 20 bar above the steam pressure of pure water at the temperature employed. For example at a temperature of 160°C. there is preferably employed a pressure of 8 to 10 bar. The carbon dioxide formed in the reaction serves suitable to regulate the pressure.

For carrying out the process of the invention there generally are added aqueous solutions of 5-(2-methylmercaptoethyl)-hydantoin, preferably solutions containing 10 to 30 weight percent of the hydantoin. Instead of the hydantoin there can be used directly the reaction mixture obtained in producing the hydantoin from 3-methylmercaptopropionaldehyde, hydrogen cyanide, ammonia and carbon dioxide.

The reaction is advantageously carried out in the presence of ammonia. Of course ammonia is formed during the course of the reaction. However, it is favorable if ammonia is already present to a considerable amount at the beginning of the reaction and it is therefore suitable to add a hydantoin solution which contains ammonia, especially one containing 0.1 to 2.0 moles of ammonia per mole of the hydantoin.

Besides this, it is advantageous to use a hydantoin solution which contains methionine, especially about 0.1 to 5.0 moles of methionine, preferably 0.5 to 1.5 moles of methionine per mole of the hydantoin.

The 3,6-bis-(2-methylmercaptoethyl)-2,5-piperazinedione generally separates as a solid from the reaction mixture if this is cooled to about room temperature. The precipitating piperazinedione in most cases is so pure without treatment, that it is suited directly for further working for example to methionyl-methionine. The remaining mother liquor besides residual piperazinedione contains ammonia and methionine, which in a given case is formed as byproduct in the reaction. The mother liquor with advantage is used in place of water for the preparation of the starting solution for a further charge.

It is especially favorable to choose a procedure in which the mother liquor is continuously recycled. In this case the reaction mixture resulting from the production of the hydantoin with advantage is used directly and is continuously fed into the cycle.

In the examples the gas volumes are calculated based on "normal conditions" (0°C. and 1 bar). The percentages set forth are weight percent.

EXAMPLE 1

In a 3 liter autoclave containing 150 grams of methionine dissolved in 1150 ml of water there were added 590 grams of a 29.6% aqueous solution of a technically pure 5-(2-methylmercaptoethyl)hydantoin warmed to 60°C. The mixture was then held with stirring for 5 hours at 160°C. In the first three hours the pressure was up to 9.5 bar and in the following 2 hours the pressure was 7.5 to 8.5 bar. At about 20 minute intervals the pressure was lowered by opening a control valve, namely in the first 3 hours each time to 8.5 bar and in the following 2 hours each time to 7.2 bar. Hereby the process was so controlled that only carbon dioxide but not steam and ammonia developed. Altogether 21.5 liters of carbon dioxide was drawn off. Upon cooling the reaction mixture the 3,6-bis-(2-methylmercaptoethyl)-2, 5-piperazinedione crystallized out. This was filtered under suction, digested with 250 ml of water at 40°C., again filtered under suction and then dried at 90°C. in a vacuum-drier. The yield was 102 grams, corresponding to 78% based on the hydantoin employed. The mother liquor combined with the wash water was concentrated to 1150 ml. It contained 150 grams of methionine and was directly usable for a further charge.

EXAMPLE 2

The procedure was the same as in Example 1 but by opening the control valve the pressure was first lowered to 6.8 bar and in the further course of the reaction to 6.3 whereby in all there escaped besides 2.0 liters of carbon dioxide 6.3 grams of ammonia as well as steam. The yield of 3,6-bis-(2-methylmercaptoethyl)-2, 5-piperazinedione amounted to 36 grams corresponding to 28% based on the hydantoin employed. The mother liquor contained besides 150 grams of methionine 125 grams of unreacted hydantoin.

EXAMPLE 3

The procedure was the same as in Example 1 except there were employed 174 grams of chemically pure 5-(2-methylmercaptoethyl)-hydantoin. In all there escaped 19.5 liters of carbon dioxide. The yield of 3,6-bis-(2-methylmercaptoethyl)-2,5-piperazinedione amounted to 109 grams, corresponding to 83% based on the hydantoin employed.

EXAMPLE 4

The product obtained by the reaction of 52 grams of 3-methylmercaptopropionaldehyde with 14.5 grams of hydrogen cyanide, 14 grams of ammonia and 26 grams of carbon dioxide was diluted with water to 400 grams of an aqueous solution and then held in a 2 liter autoclave with stirring for 4 hours at 175°C. In the course of this time there escaped through several openings of the control valves and lowering of the pressure each time to 9.5 bar a total of 11.9 liters of carbon dioxide. The rest of the procedure was as in Example 1. The yield of 3,6-bis-(2-methylmercaptoethyl)-2,5-piperazinedione amounted to 26 grams, corresponding to 40%, based on the 3-methylmercaptopropionaldehyde employed. The mother liquor was concentrated to 250 ml and was used in place of water for a subsequent charge. The yield of 3,6-bis-(2-methylmercaptoethyl)-2,5-piperazinedione amounted in this charge to 54 grams, corresponding to 82% based on the 3-methylmercaptopropionaldehyde employed.

EXAMPLE 5

The procedure was the same as in Example 1 except that there were added 295 grams of a 30% aqueous solution of 5-(2-methylmercaptoethyl)-hydantoin to a 2 liter autoclave containing 600 ml of water having 8.5 grams of ammonia and 75 grams of methionine dissolved therein. The yield of 3,6-bis-(2-methylmercaptoethyl)-2,5-piperazinedione was 56 grams, corresponding to 85% based on the hydantoin employed.

The process can comprise, consist essentially of or consist of the steps set forth.

We claim:

1. A process for the production of 3,6-bis-(2-methylmercaptoethyl)-2,5-piperazinedione comprising heating 5-(2-methylmercaptoethyl)-hydantoin in the presence of water to a temperature of 100° to 200 °C. at an elevated pressure.

2. The process according to claim 1 wherein the pressure is at least 0.2 bar above the vapor pressure of pure water at the temperature of reaction.

3. The process of claim 2 wherein the pressure is 0.5 to 20 bar above the vapor pressure of pure water at the temperature of reaction.

4. The process of claim 3 wherein the hydantoin solution employed contains ammonia.

5. The process of claim 4 wherein the hydantoin solution employed contains methionine.

6. The process of claim 2 wherein the hydantoin solution employed contains 0.1 to 2.0 moles of ammonia per mole of hydantoin.

7. The process of claim 2 wherein the hydantoin solution employed contains methionine.

8. The process of claim 7 wherein the methionine is employed in an amount of 0.1 to 5.0 moles per mole of hydantoin.

9. The process of claim 8 wherein the methionine is employed in an amount of 0.5 to 1.5 moles per mole of hydantoin.

10. The process of claim 2 wherein the piperazinedione formed is crystallized out of the reaction mixture and the mother liquor is concentrated and recycled to form starting material for another batch.

11. The process of claim 1 wherein the hydantoin employed is formed in situ from 3-methylmercaptopropionaldehyde, hydrogen cyanide, ammonia and carbon dioxide.

12. The process of claim 1 wherein the pressure is at least 0.2 bar above the vapor pressure of pure water at the temperature of reaction, the hydantoin solution contains 0.1 to 2.0 moles of ammonia per mole of hydantoin and the hydantoin solution contains methionine in an amount of 0.1 to 5.0 moles per mole of hydantoin.

* * * * *